(12) United States Patent
Inoue et al.

(10) Patent No.: US 6,439,059 B1
(45) Date of Patent: Aug. 27, 2002

(54) METHOD OF PREDICTING BENDING LIFE OF ELECTRIC WIRE OR ELECTRIC WIRE BUNDLE

(75) Inventors: Takuya Inoue; Yuki Kawakita, both of Mie; Hiroshi Kawauchi; Kouji Ohuchi, both of Osaka, all of (JP)

(73) Assignees: Sumitomo Wiring Systems, Ltd., Yokkaichi; Sumitomo Electric Industries, Ltd., Osaka, both of (JP)

( * ) Notice: Subject to any disclaimer, the term of this patent is extended or adjusted under 35 U.S.C. 154(b) by 0 days.

(21) Appl. No.: 09/787,412
(22) PCT Filed: Jul. 24, 2000
(86) PCT No.: PCT/JP00/04934
§ 371 (c)(1), (2), (4) Date: Sep. 10, 2001
(87) PCT Pub. No.: WO01/08172
PCT Pub. Date: Feb. 1, 2001

(30) Foreign Application Priority Data

Jul. 26, 1999 (JP) .......................................... 11-210650

(51) Int. Cl.$^7$ ................................................ G01N 3/32
(52) U.S. Cl. ...................................................... 73/812
(58) Field of Search ........................ 73/808, 810, 812, 73/814, 815, 849, 851, 852, 853

(56) References Cited

U.S. PATENT DOCUMENTS 4,002,061 A * 1/1977 Smith et al. ................. 361/280
4,979,396 A * 12/1990 Carder et al. ................. 73/812
5,699,274 A * 12/1997 Starostovic, Jr. ............ 702/113
5,945,594 A * 8/1999 Kendig et al. .............. 204/404

FOREIGN PATENT DOCUMENTS

JP          8-166333          6/1996

OTHER PUBLICATIONS

English Language Abstract of JP 8–166333.

* cited by examiner

Primary Examiner—Max Noori
(74) Attorney, Agent, or Firm—Greenblum & Bernstein, P.L.C.

(57) ABSTRACT

A master curve indicating correlation between a bending life and a distortional change quantity of a wire is previously acquired. The master curve is acquired by repetitively bending a single wire and analyzing (CAE analysis with a computer or the like) a distortional change quantity ($\Delta\epsilon$) of the surface of its insulating layer while actually measuring the bending life. Then, the distortional change quantity ($\Delta\epsilon$) of the surface of the insulating layer of the wire or the like regarded as the object for predicting the bending life is calculated (CAE analysis or the like). The bending life of the wire or the like is predicted by collating the calculated distortional change quantity ($\Delta\epsilon$) of the wire or the like serving as the prediction object with the aforementioned master curve. The bending life can be correctly predicted regardless of product conditions of the wire or the like.

6 Claims, 4 Drawing Sheets

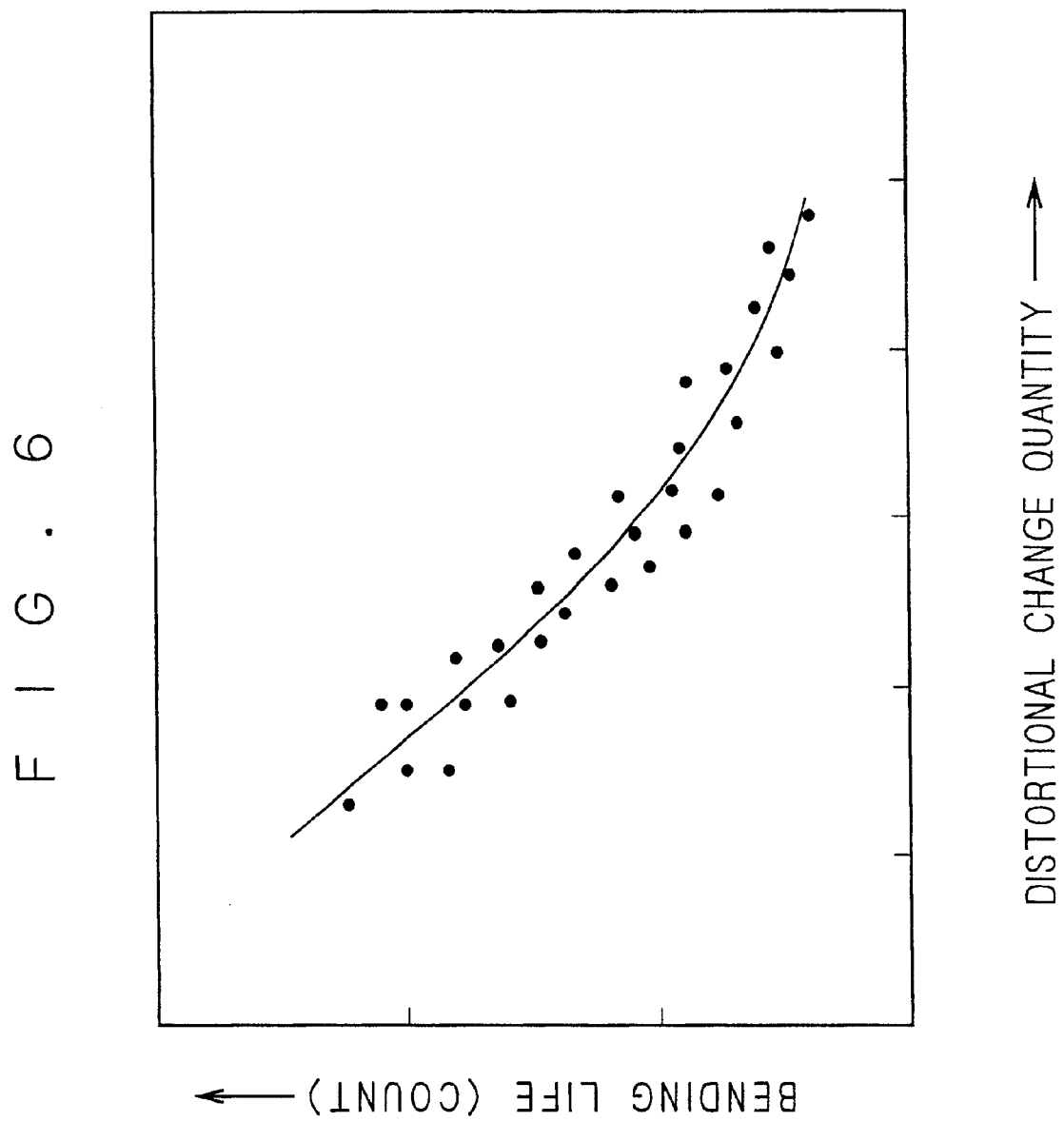

METHOD OF PREDICTING BENDING LIFE OF ELECTRIC WIRE OR ELECTRIC WIRE BUNDLE

TECHNICAL FIELD

The present invention relates to a method of predicting the bending life of wires, which are formed by coating conductor wires with insulating layers, supplying electric signals of an automobile and an industrial apparatus and electric-electronic apparatuses mounted thereon and power from a power source or a wire harness (wire harness) thereof up to disconnection caused by bending.

BACKGROUND TECHNIQUE

As is well known, a large number of wires are used for an automobile or an industrial apparatus. Among the wires or a wire harness prepared by bundling a plurality of wires (the wires and the wire harness are hereinafter generically referred to as "wire or the like"), there is a one arranged on a position such as a door portion or a seat portion of an automobile subjected to bending, for example, and such a wire or the like may lead to disconnection when repetitively subjected to bending deformation.

Therefore, it is important to evaluate bendability of the wire or the like, and a certain degree of bending life (the count of bending of the wire or the like leading to disconnection caused by bending) has been experimentally predicted from the degree of bending or the like in general. Particularly when the bendability has been regarded as important, the bending life has been evaluated by making a test in practice every time product conditions have been changed.

However, correct and objective evaluation cannot be performed when experimentally predicting the bending life, while it follows that a great deal of cost and time are required for designing the wire harness when making a test in practice every time the product conditions are changed.

Therefore, development of a method of predicting the bending life of a wire or the like on the basis of a theoretical basis is desired, and a technique disclosed in Japanese Patent Application Laid-Open No. 8-166333, for example, has been proposed. According to such a technique, the bending life is predicted on the basis of the maximum distortion quantity of a conductor part of a wire. However, it is only a single feeder such as a flat wire that allows calculation of the maximum distortion quantity, and this cannot be applied to a general wire (wire formed by stranding a conductor part).

DISCLOSURE OF THE INVENTION

Object of the Invention

The present invention has been proposed in consideration of the aforementioned subject, and the object thereof is to provide the bending life prediction method for a wire or a wire harness which can correctly predict its bending life regardless of product conditions of the wire or the like.

Structure and Function of the Invention

The present invention is a bending life prediction method for a wire for predicting the bending life of a wire, formed by coating a conductor wire with an insulating layer, up to disconnection caused by bending, which comprises a step of repetitively bending a wire (1) for previously obtaining correlation between its distortional change quantity and an actually measured value of the bending life, a step of calculating a distortional change quantity ($\Delta\epsilon$) of the wire (1) serving as the prediction object, and a step of predicting the bending life of the prediction object wire by collating the said distortional change quantity ($\Delta\epsilon$) of the prediction object wire as calculated with the said correlation.

Or, it is a bending life prediction method for a wire harness for predicting the bending life of a wire harness (2), prepared by bundling a plurality of wires formed by coating conductor wires with insulating layers, up to disconnection caused by bending, which comprises a step of repetitively bending the wires forming the said wire harness (2) for previously obtaining correlation between its distortional change quantity and an actually measured value of the bending life, a step of calculating a distortional change quantity ($\Delta\epsilon$) of the wire harness (2) serving as the prediction object, and a step of predicting the bending life of the prediction object wire harness by collating the said distortional change quantity ($\Delta\epsilon$) of the prediction object wire harness as calculated with the said correlation.

Desirably, the step of obtaining the said correlation obtains the said correlation by repetitively bending the said wire as to a plurality of distortional change quantities ($\Delta\epsilon$) and actually measuring the count of bending up to disconnection.

Desirably, the step of obtaining the said correlation obtains the said correlation by executing the said measurement every temperature.

When predicting the bending life of the said wire (1) at this point, the said distortional change quantity ($\Delta\epsilon$) is calculated by the following equation in the step of calculating the said distortional change quantity ($\Delta\epsilon$) of the prediction object wire serving as the prediction object on the assumption that r represents the radius of the said wire (1), $R_1$ represents the bend radius of the said wire (1) in a state most bent on a position bent/changed at the maximum within a region of the said wire (1) subjected to bending and $R_2$ represents the bend radius of the said wire (1) in a most elongated state:

$$\Delta\epsilon = r \cdot (1/R_1 - 1/R_2)$$

Thus, the bending life of the prediction object wire is predicted by repetitively bending the wire for previously obtaining the correlation between its distortional change quantity and the actually measured value of the bending life and thereafter calculating the distortional change quantity of the wire serving as the prediction object and collating the calculated distortional change quantity of the prediction object wire with the aforementioned correlation, whereby the bending life can be correctly predicted regardless of the product conditions of the wire.

Or, when predicting the bending life of the wire harness (2), the step of obtaining the said correlation obtains the said correlation as to a single wire by repetitively bending the said wire as to a plurality of distortional change quantities ($\Delta\epsilon$) and actually measuring the count of bending up to disconnection, for calculating the said distortional change quantity ($\Delta\epsilon$) by the following equation in the step of calculating the said distortional change quantity ($\Delta\epsilon$) of the said wire harness (2) serving as the prediction object by supposing a single virtual wire member formed by weighted-averaging the said conductor wires and the said insulating layers by a sectional area ratio, regarding the virtual wire member as single said wire and assuming that r represents the radius of the said virtual wire member, $R_1$ represents the bend radius of the said virtual wire member in a state most bent on a position bent/changed at the maximum within a region of the said virtual wire member subjected to bending and $R_2$ represents the bend radius of the said virtual wire member in a most elongated state:

$$\Delta\epsilon = r \cdot (1/R_1 - 1/R_2)$$

Thus, the bending life of the prediction object wire harness is predicted by repetitively bending a single wire forming the wire harness for previously obtaining correlation between its distortional change quantity and the actually measured value of the bending life and thereafter collating the calculated distortional change quantity of the prediction object wire harness with the aforementioned correlation, whereby the bending life can be correctly predicted regardless of product conditions of the wire harness.

Other objects and features of the present invention are clarified in the following description.

BRIEF DESCRIPTION OF THE DRAWINGS

FIG. 6 is a diagram showing results of collation with a master curve as to the wire harness of FIG. 4.

BEST MODES FOR CARRYING OUT THE INVENTION

First Embodiment

First, the basic idea of the present invention is described. The inventors have made deep study as to factors dominating the bending life of a wire or the like. Consequently, they have clarified that disconnection of the wire or the like is mainly dominated by fatigue failure of an insulating layer coating a conductor part and the fatigue failure of the insulating layer has strong correlation with a change quantity of its surface distortion since, when cracking takes place due to the fatigue failure of the insulating layer, local stress is readily applied to the conductor part of the portion causing the cracking particularly under a low temperature. That is, they have obtained such recognition that strong correlation is present between the bending life of the wire or the like and the distortional change quantity of the surface of the insulating layer at the time of bending change. When set on a door portion, a seat portion or the like of an automobile in practice, however, the wire is set in various shapes such as an S shape and a U shape. The manner of application of stress to a wire 1 also varies with its shape. The way of application of stress to the wire 1 varies with its shape. However, they have also obtained such recognition that the correlation between the bending life and the distortional change quantity of the wire or the like is not dependent on the shape of the wire or the like but constant in wide-ranging bent shapes although the wire 1 is set in various shapes.

When experimentally obtaining the correlation between the bending life and the distortional change quantity of the wire, therefore, it follows that the bending life of the wire or the like can be predicted by simply analyzing the distortional change quantity as to the wire or the like under various product conditions. The present invention has been completed on the basis of such recognition, and the concrete bending life prediction method is now described.

Figure 1:
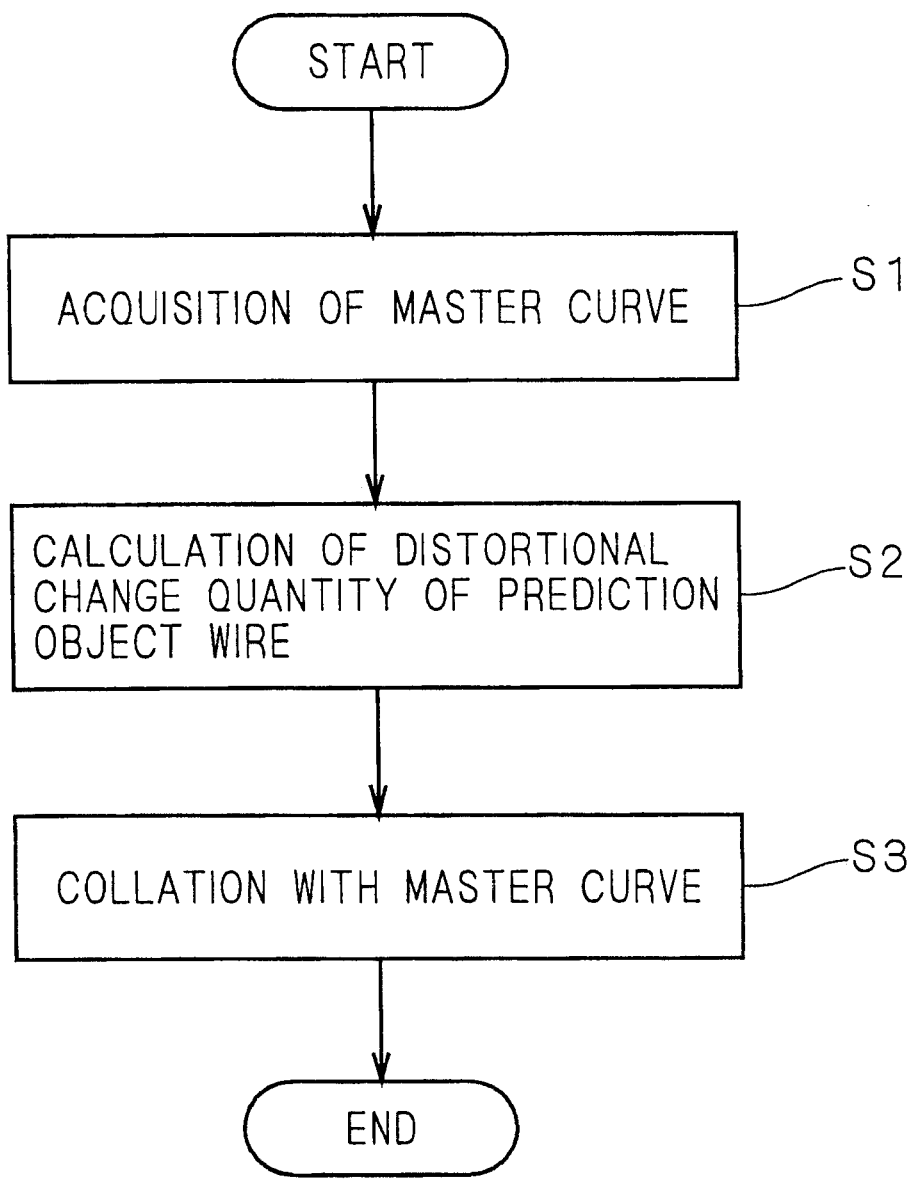
FIG. 1 is a flow chart showing the procedure of a bending life prediction method for a wire or the like according to the present invention.

FIG. 1 is a flow chart showing the procedure of the bending life prediction method for a wire or the like according to the present invention. First, a master curve indicating the correlation between the bending life and the distortional change quantity of the wire is previously acquired (step S1). The master curve is acquired by repetitively bending a single wire, analyzing its distortional change quantity by CAE analysis or the like, for example, and actually measuring the bending life as to various distortional change quantities.

Figure 2:
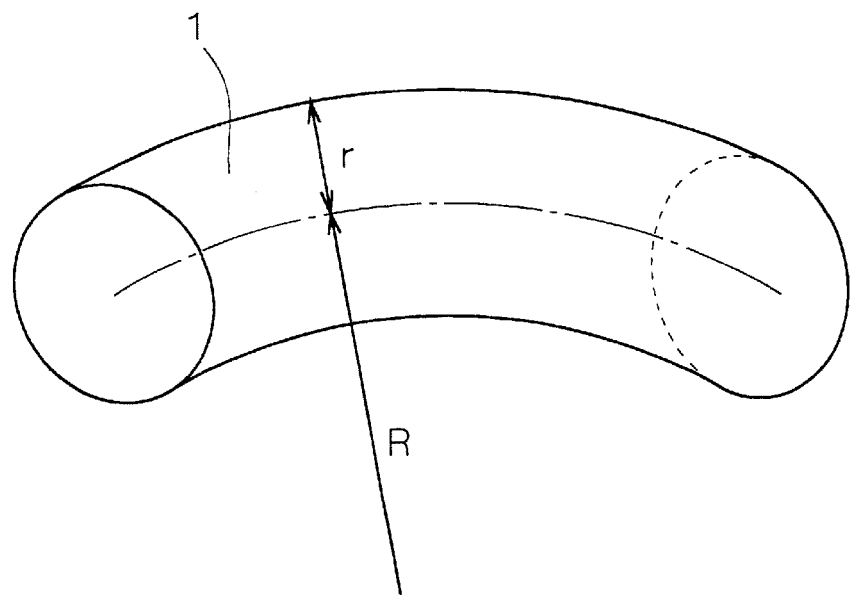
FIG. 2 is a diagram for illustrating a distortional change quantity of a wire.

FIG. 2 is a diagram for illustrating the distortional change quantity of the wire. It is assumed that r represents the radius of the wire 1 formed by coating a conductor wire with an insulating layer. The wire 1 is subjected to bending deformation, and the curvature K is expressed as $K=1/R$ assuming that R represents its bend radius. Distortion $\epsilon$ caused on the surface of the insulating layer of the wire 1 is expressed in the following equation {1} at this time:

$$\epsilon = 2\pi(R+r)/2\pi R - 1$$
$$= (R+r)/R - 1 \qquad \{1\}$$

Assuming here that, in the wire 1 arranged on a position of a door portion, a seat portion or the like subjected to bending, $R_1$ represents the bend radius of the wire 1 in a state most bent on the position subjected to bending, $R_2$ represents the bend radius of the wire 1 in a most elongated state and $\Delta\epsilon$ represents the distortional change quantity of the surface of the insulating layer at the time of repetitively bending the wire 1 between the most bent state and the most elongated state, $\Delta\epsilon$ is expressed in the following equation {2}:

$$\Delta\epsilon = (R_1+r)/R_1 - (R_2+r)/R_2$$
$$= r \cdot (1/R_1 - 1/R_2)$$
$$= r \Delta K \qquad \{2\}$$

In the equation {2}, $\Delta K$ represents a change quantity of the curvature at the time of repetitively bending the wire 1, which can be calculated by analysis (the so-called CAE analysis (computer-aided engineering)) with a computer from shape change of the wire 1 at the time of the repetitive bending. The distortional change quantity $\Delta\epsilon$ of the surface of the insulating layer can be obtained from the equation {2} by listing up the calculated $\Delta K$ as to each portion of the wire 1 and employing $\Delta K$ having the maximum value.

On the other hand, the bending life is obtained by repetitively bending the wire 1 and measuring the count of bending up to disconnection in practice. As hereinabove described, disconnection of the wire or the like under a low temperature is mainly dominated by fatigue failure of the insulating layer coating the conductor part, and the bending life has temperature dependency. Therefore, it follows that measurement of the bending life is performed every necessary temperature.

Figure 3:
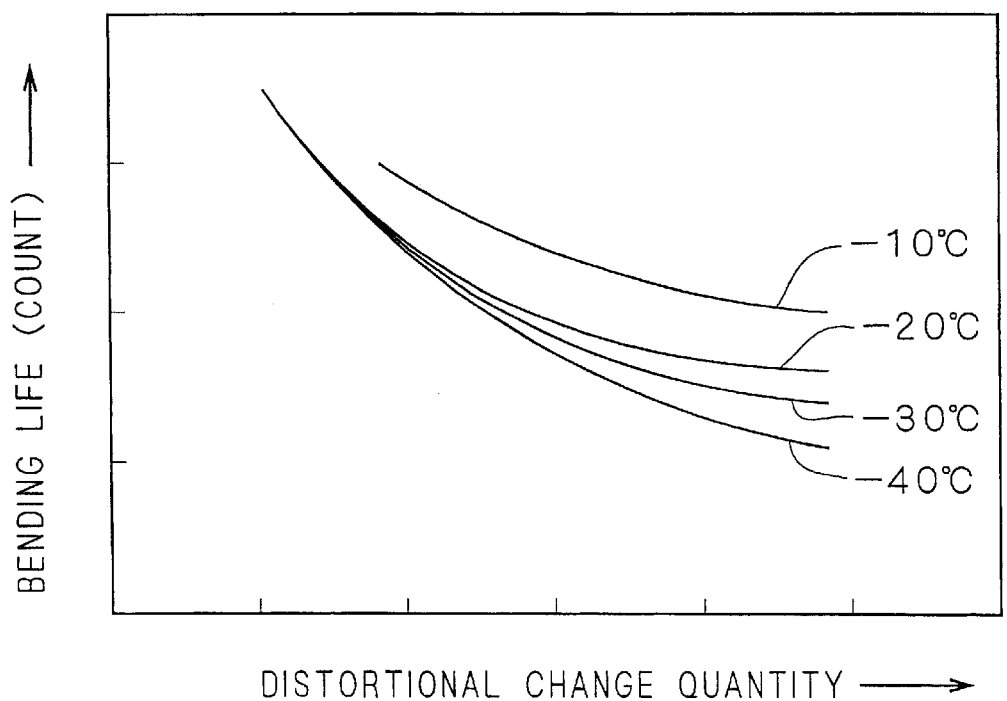
FIG. 3 is a diagram showing examples of obtained master curves.

FIG. 3 is a diagram showing examples of obtained master curves. The horizontal axis of the figure shows distortional change quantities of the surface of the insulating layer, and the vertical axis shows bending lives. As shown in FIG. 3, bendability lowers as the temperature lowers, i.e., the bending life at the same distortional change quantity shortens.

Referring again to FIG. 1, the process advances to a step S2 after acquiring the master curve, for calculating the distortional change quantity of the wire or the like regarded as the object for predicting the bending life. The distortional change quantity of the wire or the like regarded as the prediction object is basically obtained by an idea similar to that described with reference to FIG. 2. Concretely, the distortional change quantity of the wire or the like regarded as the prediction object is calculated by shape simulation with a computer, and calculated by CAE analysis on the basis of the mounted state and the mounted shape of the wire or the like and the mode of bending deformation applied after mounting or the like. The distortional change quantity calculated at this point is the distortional change quantity of the surface of the insulating layer coating the conductor part, similarly to the time acquiring the master curve.

Then, the calculated distortional change quantity of the wire or the like serving as the prediction object is collated with the aforementioned master curve (FIG. 3) thereby predicting the bending life of the wire or the like (step S3). As already described, the correlation between the bending life and the distortional change quantity of the wire or the like itself is not dependent on the shape of the wire or the like. When the distortional change quantity of the wire or the like can be calculated, therefore, its bending life can be correctly predicted regardless of the product conditions of the wire or the like (for example, whether it is a single wire or a wire harness formed by a plurality of wires, whether it is a flat wire or a wire formed by stranding a conductor part, the mounted state and the mounted shape etc.). This does not mean that the bending life prediction method for a wire or the like according to the present invention gives absolutely no consideration to the product conditions of the wire or the like, but they are taken into consideration in the stage of calculating the distortional change quantity of the wire or the like regarded as the prediction object.

Thus, the bending life can be correctly predicted regardless of the product conditions of the wire or the like, whereby desk study is enabled beforehand by reflecting the prediction result on design of the wire harness or the like for attaining optimum design and reduction of the development period. Further, the number of tests performed in practice for bending life measurement can be reduced.

While an embodiment of the present invention has been described, an embodiment concretely embodying this is now described. While the aforementioned equation {2} and FIG. 3 are adapted as to the wire 1 formed by coating the periphery of a single conductor part with the insulating layer, this is further applied and a case of predicting the bending life of a wire harness having the structure of a wire harness applied to a door portion of an automobile is described at this point as an example.

Figure 4:
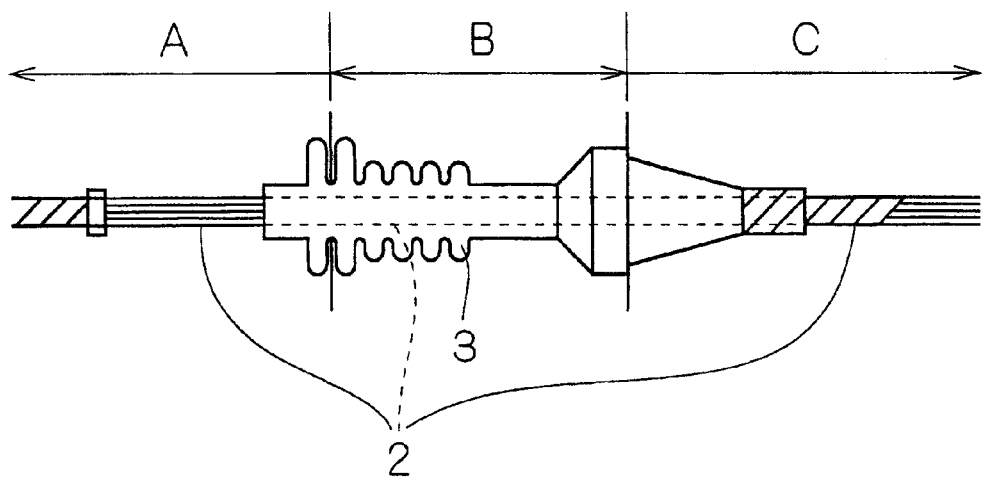
FIG. 4 is a diagram showing a wire harness used for a door portion of an automobile.

FIG. 4 is a diagram showing the wire harness used for the door portion of the automobile. This wire harness 2 is employed as a wiring electrically connecting an electric apparatus in the inner part of the door and the body of the automobile with each other. Therefore, a region A arranged in the door, a region C arranged in the body and a region B arranged between the door and the body are present in the wire harness 2. As to the region B of the wire harness 2 among these, a grommet 3 is provided since it is a region repetitively subjected to bending deformation and exposed to the air when the door is opened and closed. The region B of the wire harness 2 is the region having the possibility of leading to disconnection by repetitive bending deformation, and serves as the object for predicting the bending life.

Figure 5:
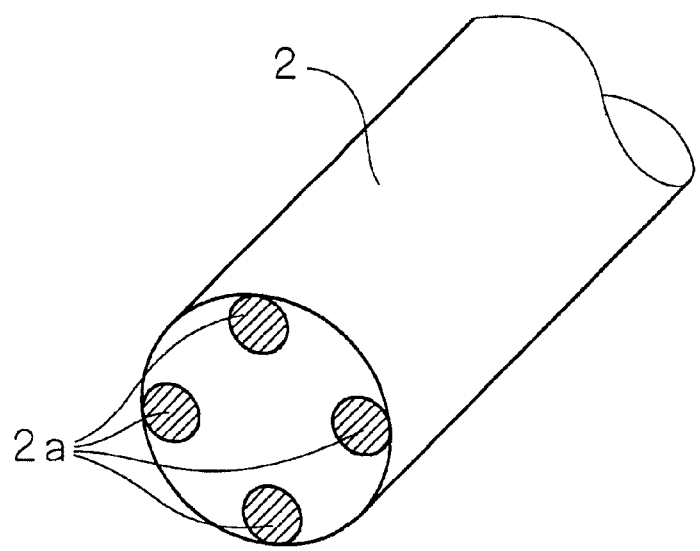
FIG. 5 is a diagram showing a state of division at the time of analyzing a distortional change quantity of the wire harness of FIG. 4.

When predicting the bending life of the wire harness 2, the distortional change quantity is calculated as to the region B of the wire harness 2. The distortional change quantity of the region B of the wire harness 2 is calculated by CAE analysis on the basis of the mounted states of the wire harness 2 to the door and the body and its shape, the mode of bending deformation applied to the wire harness 2 when the door is opened and closed, and the position and the length of the grommet 3 etc. At this point, the wire harness 2 is a wire harness prepared by bundling a plurality of wires as described above and has a certain degree of thickness, and hence four potions of its surface are set as shown in FIG. 5, for performing CAE analysis as to the respective portions 2a. In this CAE analysis, further, a virtual material prepared by weighted-averaging the bending elastic coefficients of a metal material for the conductor part and an insulating material for the coating layer with the sectional area ratio thereof and averaging the metal material for the conductor part and the insulating material for the coating layer is supposed. Such a virtual material is assumed to be a single wire member (hereinafter referred to as "virtual wire member") for supposing the radius r of the virtual wire member and its bend radius R (FIG. 2) and calculating the distortional change quantity ($\Delta\epsilon$ in the equation {2}) of the wire harness 2 in consideration of $R_1$ (the bend radius of the virtual wire member in the most bent state) and $R_2$ (the bend radius of the virtual wire member in the most elongated state) shown in the equation {2}. While various distortional change quantities are listed up by the CAE analysis at this time, the distortional change quantity exhibiting the maximum value is employed.

Then, the distortional change quantity of the wire harness 2 calculated and employed through the CAE analysis is collated with a master curve. The master curve is previously acquired as to a single wire forming the wire harness 2 as that indicating the correlation between the bending life and the distortional change quantity thereof. At this point, it is assumed that a master curve similar to any of FIG. 3 is obtained.

FIG. 6 is a diagram showing results of collation with the master curve as to the wire harness 2. This master curve shows the correlation between the bending life and the distortional change quantity in a $-30°$ C. atmosphere as to the single wire forming the wire harness 2 (identical to the master curve of $-30°$ C. in FIG. 3). Black points in the figure are results actually measured as to the bending life of the wire harness 2. The results obtained by making collation with the master curve and the results of actual measurement excellently match with each other as shown in FIG. 6, and it has been confirmed that the bending life of the wire or the like can be correctly predicted by the method according to the present invention.

While this embodiment has been carried out as to the wire harness 2 which is a wire harness prepared by bundling a plurality of wires, it is needless to say that a single wire also excellently matches with the master curve and its bending life can be correctly predicted.

While each embodiment of the invention has been described, the scope of the present invention is not restricted to the aforementioned embodiment but defined by the appended scope of claim.

What is claimed is:

1. A bending life prediction method for a wire, formed by coating a conductor wire with an insulating layer, said method predicting the bending life of a wire up to disconnection caused by bending and comprising:

repetitively bending a wire to obtain correlation between its distortional change quantity and an actually measured value of the bending life;

calculating a distortional change quantity (Δε) of said wire serving as the prediction object based on the radius of said wire and its bend radius; and predicting the bending life of said prediction object wire by collating said distortional change quantity (Δε) of the prediction object wire as calculated with said correlation.

2. The bending life prediction method according to claim 1, wherein obtaining said correlation obtains said correlation by repetitively bending said wire as to a plurality of distortional change quantities (Δε) and actually measuring the count of bending up to disconnection.

3. The bending life prediction method according to claim 1, wherein said correlation obtains said correlation by executing said measurement every temperature.

4. The bending life prediction method according to claim 1, calculating said distortional change quantity (Δε) by the following equation in the step of calculating said distortional change quantity (Δε) of said wire serving as the prediction object assuming that r represents the radius of said wire, $R_1$ represents the bend radius of said wire in a state most bent on a position bent/changed at the maximum within a region of said wire subjected to bending and $R_2$ represents the bend radius of said wire in a most elongated state:

$$\Delta\epsilon = r(/R_1 - 1/R_2).$$

5. A bending life prediction method for a wire harness prepared by bundling a plurality of wires formed by coating conductor wires with insulating layers, said method predicting the bending life of a wire harness up to disconnection caused by bending and comprising:

repetitively bending the wires forming said wire harness to obtain correlation between its distortional change quantity and an actually measured value of the bending life;

calculating distortional change quantity (Δε) of the wire harness serving as the prediction object based on the correlation between its distortional change and the measured value of the bending life; and predicting the bending life of said prediction object wire harness by collating said distortional change quantity (Δε) of the prediction object wire harness as calculated with said correlation.

6. The bending life prediction method according to claim 5, wherein obtaining said correlation obtains said correlation as to a single wire by repetitively bending the wire in the above as to a plurality of distortional change quantities Δε) and actually measuring the count of bending up to disconnection, for calculating said distortional change quantity (Δε) by the following equation in the step of calculating said distortional change quantity (Δε) of said wire harness serving as the prediction object by supposing a single virtual wire member formed by weighted-averaging said conductor wires and said insulating layers by a sectional area ratio, regarding said virtual wire member as a single said wire and assuming that r represents the radius of said virtual wire member, $R_1$ represents the bend radius of said virtual wire member in a state most on a position bent/changed at the maximum within a region of said virtual wire member subjected to bending and $R_2$ represents the bend radius of said virtual wire member in a most elongated state:

$$(\Delta\epsilon) = r(1/R_1 - 1/R_2).$$

* * * * *